United States Patent [19]
Guthrie et al.

[11] Patent Number: 5,288,696
[45] Date of Patent: Feb. 22, 1994

[54] METHOD FOR PRODUCING AND CLONING SACII RESTRICTION ENDONUCLEASE AND METHYLASE

[75] Inventors: Ellen P. Guthrie, Swampscott; Marta M. Meda, Beverly, both of Mass.

[73] Assignee: New England Biolabs, Inc., Beverly, Mass.

[21] Appl. No.: 578,822

[22] Filed: Sep. 7, 1990

[51] Int. Cl.$^5$ .................. C12N 9/10; C12N 15/54; C12N 15/70; C12N 15/76
[52] U.S. Cl. .................. 435/199; 455/69.1; 455/752.31; 455/252.35; 455/320.1; 536/73.2; 935/9; 935/14; 935/29; 935/73; 935/74
[58] Field of Search .............. 435/69.1, 172.1, 252.3, 435/252.35, 320.1, 199, 172.3, 127.3, 252.31; 536/27

[56] References Cited

U.S. PATENT DOCUMENTS

| | | | |
|---|---|---|---|
| 4,791,064 | 12/1988 | Fare et al. | 435/252.3 |
| 4,843,002 | 6/1989 | Rao et al. | 435/172.3 |
| 4,879,241 | 11/1989 | Birmingham et al. | 435/253.5 |
| 4,898,828 | 2/1990 | Heushberger et al. | 435/252.3 |
| 4,914,030 | 4/1990 | Schoner et al. | 435/172.3 |
| 4,918,015 | 4/1990 | Wohlleber et al. | 435/172.3 |
| 4,983,522 | 1/1991 | Barsonian et al. | 435/172.3 |
| 4,983,542 | 1/1991 | Van Cott et al. | 435/172.3 |
| 4,988,620 | 1/1991 | Van Cott et al. | 435/199 |
| 4,996,151 | 2/1991 | Brooks et al. | 435/172.3 |
| 4,999,293 | 3/1991 | Barsomian et al. | 435/172.3 |
| 5,015,581 | 5/1991 | Benner, II et al. | 435/172.3 |
| 5,024,948 | 6/1991 | Rothstein et al. | 435/252.1 |
| 5,030,569 | 7/1991 | Lunnen et al. | 435/172.3 |
| 5,049,501 | 9/1991 | Katsaragi et al. | 435/199 |
| 5,053,330 | 10/1991 | Lunnen et al. | 435/172.3 |
| 5,082,784 | 1/1992 | Chatterjee et al. | 435/252.3 |
| 5,100,793 | 3/1992 | Morgan | 435/172.3 |
| 5,137,823 | 8/1992 | Brooks | 435/199 |
| 5,139,942 | 8/1992 | Benner | 435/199 |
| 5,194,387 | 3/1993 | MacNeil | 435/320.1 |

FOREIGN PATENT DOCUMENTS 0248678 12/1987 European Pat. Off. .
0332406 9/1989 European Pat. Off. .
0193413 3/1986 PCT Int'l Appl. .

OTHER PUBLICATIONS

Endow, et al. J. Mol. Biol., 112:521 (1977).
Waalwijk, et al., Nucleic Acids Res., 5:3231 (1978).
Gingeras and Brooks, Proc. Nat. Acad. Sci. 80:402 (1983).
Mann, et al., Cell 3:97–112 (1978).
Kosykh, et al., Molec..Gen. Genet. 178:717 (1980).
Walder, Proc. Nat. Acad. Sci., 78:1503 (1981).
Bougueleret, et al., Nuc. Acids. Res. 12:3659 (1984).
Theriault and Roy, Gene, 19:355 (1982).
Blumenthal, et al., J. Bacteriol. 164:501 (1985).
Howard, et al., Nucl. Acids. Res. 14:7939 (1988).
Wilson, Trends in Genetics 4:314 (1988).
Lunnen, Gene 74:25 (1988).
Chandrasegeran, et al. Structure and Expression, vol. I, pp. 149–156 (1988).
Brooks, et al., Gene 74:13 (1988).
Barnes, G., and Rine, J., 1985, Proceedings of the National Academy of Sciences, U.S.A., 82:1354–1358.
Kwoh, T. J., 1986, Proceedings of the National Academy of Sciences, U.S.A., 83:7713–7717.

(List continued on next page.)

*Primary Examiner*—Robert A. Wax
*Assistant Examiner*—William W. Moore
*Attorney, Agent, or Firm*—David G. Conlin; Gregory D. Williams; David S. Resnick

[57] ABSTRACT

The present invention is directed to a method for cloning and producing the SacII restriction endonuclease by 1) introducing the restriction endonuclease gene from *Streptomyces achromogenes* into a host whereby the restriction gene is expressed; 2) fermenting the host which contains the plasmid encoding and expressing the SacII restriction endonuclease activity, and 3) purifying the SacII restriction endonuclease from the fermented host which contains the plasmid encoding and expressing the SacII restriction endonuclease activity.

12 Claims, 5 Drawing Sheets

OTHER PUBLICATIONS

Herman, J., et al., 1989, Proceedings of the American Association for Cancer Research, 30:428.

Kwoh, T. J. et al., 1988, Nucleic Acids Research, 16(24):11489-11505.

Herman, J., et al., 1989, Journal of Cellular Biochemistry, *Supplement* :223.

Bibb, M. J., et al., 1982, Molecular and General Genetics, 187:265-277.

Karremon, C., et al., 1988, Journal of Bacteriology 170(6):2527-2532.

Lunnen, K. D., et al., 1989, Gene 77: 11-19.

Brooks, J. E. et al., 1989, Nucleic Acids Research 17(3):979-997.

Ito, H., et al., 1990, Nucleic Acids Research 18(13):3903-3911.

MacNeil, D. J., 1988, Journal of Bacteriology 170(12):5607-5612.

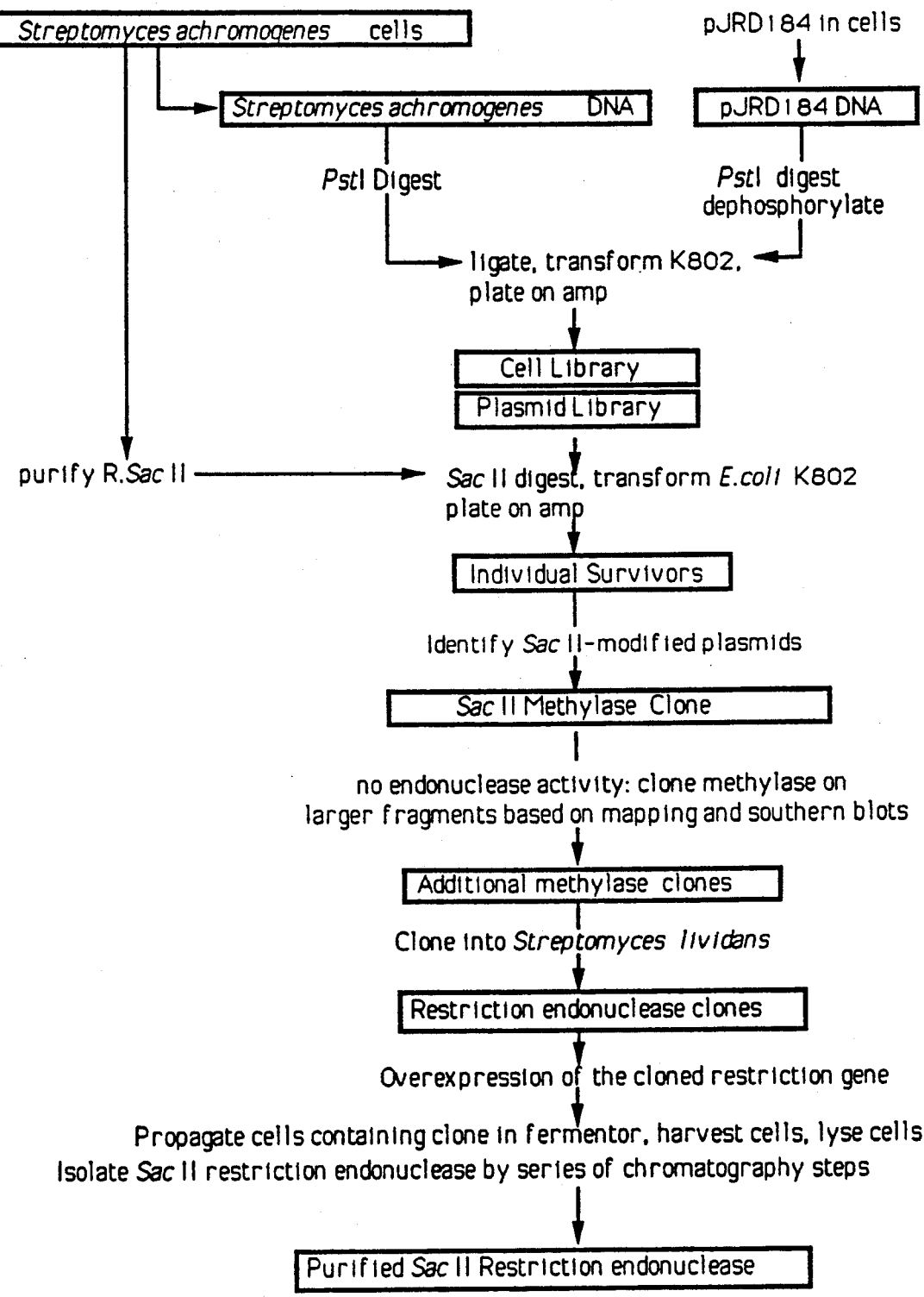
FIG. IA

METHOD FOR PRODUCING AND CLONING SACII RESTRICTION ENDONUCLEASE AND METHYLASE

BACKGROUND OF THE INVENTION

The present invention relates to recombinant DNA encoding the SacII restriction endonuclease and modification methylase, and to methods for the production of these enzymes from said recombinant DNA.

Many bacteria contain systems which guard against invasion of foreign DNA. Bacterial cells contain specific endonucleases that make double-strand scissions in invading DNA unless the DNA has been previously modified, usually by the corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Three distinct types of R-M systems have been characterized on the basis of the subunit compositions, cofactor requirements, and type of DNA cleavage. Type I R-M systems are the most complex. The endonuclease typically contains three different types of subunits and require $Mg^{++}$, ATP, and S-adenosyl-methionine for DNA cleavage. Their recognition sites are complex, and DNA cleavage occurs at non-specific sites anywhere from 400-7000 base pairs from the recognition size.

Type III R-M systems are somewhat less complex. The endonuclease of Type III R-M systems contain only two types of subunits, and although $Mg^{++}$ and ATP are required for DNA cleavage, S-adenosyl-methionine stimulates enzymatic activity without being an absolute requirement. DNA cleavage occurs distal to the recognition site by about 25-27 base pairs.

Type II R-M systems are much simpler than either Types I or III. The endonuclease only contains one subunit, and only $Mg^{++}$ is required for DNA cleavage. Moreover, the DNA cleavage site occurs within or adjacent to the enzyme's recognition site. It is this class of restriction endonucleases that has proved most useful to molecular biologists.

Bacteria usually possess only a small number of restriction endonucleases per species. The endonucleases are named according to the bacteria from which they are derived. Thus, the species *Haemophilus aegyptius*, for example, synthesizes three different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4-6 nucleotides in length. More recently, recognition endonucleases having recognition sequences of 7-8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes." Some restriction endonucleases have degenerate or relaxed specificites in that they can recognize multiple bases at the same positions. EcoRI, which recognizes the sequence GAATTC is an example of a restriction endonuclease having a symmetrical relationship, while HaeII, which recognizes the sequence PuGCGCPy, typifies restriction endonucleases having a degenerate or relaxed specificity. Endonucleases with symmetrical recognition sites generally cleave symmetrically within or adjacent the recognition site, while those that recognize asymmetric sites tend to cut at distance from the recognition site, typically from about 1-13 base pairs away from that site.

The second component of bacterial R-M systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or more of the nucleotides within the sequence by the addition of a methyl group. Following methylation, the recognition sequence is no longer bound or cleaved by the corresponding restriction endonuclease. The DNA of a bacterial cell is always modified by virtue of the activity of its modification methylase, it is therefore insensitive to the presence of the endogenous restriction endonuclease. It is only unmodified, and therefore identifiably foreign DNA that is sensitive to restriction endonuclease recognition and attack.

More than 1000 different restriction endonucleases have been isolated from bacterial strains, and many share common specificites Restriction endonucleases which recognize identical sequences are called "isochizomers." Although the recognition sequences of isochizomers are the same, they may vary with respect to site of cleavage (e.g., XmaI v. SmaI Encow et al., *J.Mol.-Biol.* 112:521 (1977) Waalwijk et al. *Nucleic Acids Res.* 5:3231 (1978)) and in cleavage rate at various sites (XhoI v. PaeR7I Gingeras et al., *Proc. Natl. Acad. Sci U.S.A.* 80:402 (1983)).

With the advent of genetic engineering technology, it is now possible to clone genes and to produce the proteins and enzymes that they encode in greater quantities than are obtainable from their natural sources by conventional purification techniques.

Type II restriction-modification systems are being cloned with increasing frequency. Four methods are being used to clone R-M systems into *E. coli* (1) subcloning of natural plasmids; (2) selection based on phage restriction; (3) selection based on vector modification; and (4) multi-step isolation.

The first cloned systems used bacteriophage infection as a means of identifying or selection restriction endonuclease clones (HhaII: Mann, et al., *Gene* 3:97-112, (1978); EcoRII: Kosykh, et al., *Molec. Gen. Genet.* 178:717-719, (1980); PstI: Walder, et al., *Proc. Nat. Acad. Sci. USA* 78:1503-1507, (1981)). Since the presence of R-M systems in bacteria enables them to resist infection by bacteriophages, cells that carry cloned R-M genes can, in principle, be selectively isolated as survivors from libraries that have been exposed to phage. This method has been found, however, to have only limited value. Specifically, it has been found that cloned R-M genes do not always manifest sufficient phage resistance to confer selective survival.

Subcloning of natural plasmids involves transferring systems initially characterized as plasmid-borne into *E. coli* cloning plasmids (EcoRV: Bougueleret, et. a., *Nucleic Acids Res.* 12:3659-3676, (1984); PaeR7: Gingeras and Brooks, *Proc. Natl. Acad. Sci. USA* 80:402-406, (1983); Theriault and Roy, *Gene* 19:355-359, (1982); PvuII: Blumental, et al., *J. Bacteriol.* 164:501-509, (1985)). In this approach the plasmids are purified prior to digestion and ligation, so reducing the complexity of the source DNA. Isolating the system then involves sub-cloning and characterizing libraries and performing selections. This approach also has a number of limitations including that most R-M systems are located on the bacterial chromosomal, not plasmids.

Vector modification, the most successful approach to date, is predicated on the assumption that the restriction and modification genes of a particular Type II system are linked and are expressed sequentially, methylase and then endonuclease. Thus, in a population of methylase positive clones, some clones should also carry the corresponding endonuclease gene. This approach, known as methylase selection, was first used successfully by Wilson, EPO Publication No. 0193413, to clone the HaeII, TaqI, BanI, HindIII, HinfI, and MspI R-M systems.

A number of R-M systems, however, have required a multi-step cloning approach. For example, during acquisition of a new R-M system, it has been found that a number of cells face an establishment problem. Unless the methylase has a head start over the endonuclease, the cell is in danger of cleaving its own cellular DNA. *E. coli* appears to cope with this problem by repairing its DNA, and is able to assimilate to many cloned R-M systems without apparent trauma. Not all systems are easily assimilated however. The DdeI and BamHI R-M systems, for example, could not be cloned in a single step; rather, three steps were required (Howard et al., *Nucleic Acids Res.* 14:7939-7951 (1988)). There are, in fact, many systems for which only the methylase gene has been cloned. These systems may be similar to BamHI and DdeI, and may require similar approaches.

While a number of clones have been obtained by one or more of the above-described methods, see, Wilson, *Gene* 74:281-289 (1988), cloning of Type II R-M systems is not without difficulty. In particular, the genetics of many R-M systems have been found to be more complex, and methylase positive clones obtained by, for example, vector modification have not yielded the corresponding endonuclease gene. See, Wilson, *Trends in Genetics* 4:314-318 (1988); Lunnen et al., *Gene* 74:25-32 (1988). In fact, numerous obstacles are encountered in the process of cloning R-M systems using vector modification. For example, in some systems, the methylase and endonuclease genes may not be linked or the endonuclease used to fragment the bacterial DNA may cut either or both of the R-M genes. In other systems, such as BamHI and DdeI, the methylase may not protect sufficiently against digestion by the corresponding endonuclease, either because of inefficient expression in the transformation host, or because of the inherent control mechanism for expression of the methylase and endonuclease genes, or for unknown reasons. Modification may also be harmful to the host cell chosen for transformation. The endonuclease sought to be cloned may not be available in sufficient purity or quantity for methylase selection. In many systems, difficulties are also encountered in expressing the endonuclease gene in a transformation host cell of a different bacterial species.

In spite of the difficulties in cloning the more complex Type II R-M systems, it has been possible to obtain some endonuclease genes by modifying the vector modification selection method (see Lunnen et al., op. cit.) and/or by using a multi-step cloning approach. For example, formation of multiple libraries, construction of new cloning vectors, use of isochizomers for the methylase selection step, mapping of methylase and/or endonuclease genes to determine the corresponding DNA sequences for use as hybridization probes, and other variations to the above-described approaches have yielded a number of recalcitrant recombinant R-M systems.

However, at the outset of any Type II R-M cloning project, one simply does not know which, if any, and what variations or modifications to previous approaches may be required to clone any particular R-M system. For example, the detailed genetics of the particular system is usually unknown. Type II R and M genes may be present on the genome in any of four possible arrangements. Wilson, *Trends in Genetics*, supra. The sizes of the enzymes, and of the corresponding genes, vary widely between one R-M system and another, as do the DNA and amino acid sequences. In fact, isochizomeric restriction endonucleases have been found to display few similarities. Id, at 318, see also Chandrasegeran et al., *Structure and Expression*, Vol. I, pp 149-156, Adenine Press (1988).

Mechanisms of control of R and M gene expression also vary widely among Type II systems. For example, expression of the endonuclease gene may be modification-dependent, as is indicated in the AvaII, HaeII, HinfI, PstI and XbaI systems. Alternatively, the endonuclease gene may contain a large number of its own recognition sites as compared to the corresponding methylase gene, as in the TaqI system. Id.

During transformation of cells to obtain clones carrying the target R-M system, cellular DNA is initially unmodified and consequently in danger of being digested by the target endonuclease. Transformation host cells must either contain DNA repair systems or be able to delay expression of the target endonuclease gene until modification is complete. If neither of these mechanisms is available to the transformation host, a problem is encountered in establishing the clones genes in the host. As noted above, when establishment problems were encountered in cloning the DdeI and BamHI systems, it was necessary to introduce the methylase and endonuclease genes sequentially, to protect the DNA of the transformation host cells (Howard, K. A. et al., supra, Brooks et al., *Gene* 74:13 (1988)). However, some R-M systems have resisted all attempts to clone them, and others have yielded only the methylase gene, possibly because of establishment difficulties. Wilson, *Trends in Genetics* 4:317.

It has been found that transformation host cells may also contain systems that restrict foreign types of modification. For example, two systems have been identified in *E. coli* which restrict modified DNAs: the mcr system restricts DNA containing methyl-cytosine, and the mrr system restricts DNA containing methyl-adenine. It is therefore usually necessary to use *E. coli* strains that are defective in these systems. The presence of additional host cell restriction systems may also be responsible for the difficulties encountered in cloning of R-M systems.

Because restriction endonucleases and modification methylases are useful tools for characterizing and rearranging DNA in the laboratory, there is a commercial incentive to produce the enzymes abundantly and in substantially pure form. Using recombinant DNA techniques in accordance with the present invention, the SacII restriction endonuclease and modification methylase may be produced simply and in commercially useful amounts.

SUMMARY OF THE INVENTION

The present invention relates to recombinant DNA encoding the genes for the SacII restriction endonuclease and modification methylase obtainable from *Streptomyces achromogenes* (ATCC No. 12767) as well as related methods for the production of these enzymes from the recombinant DNA. This invention also relates to a transformed host which expresses the restriction endonuclease SacII, an enzyme which recognizes the DNA sequence 5'-CCGCGG-3'and cleaves after the third C residue and in front of the second G residue, leaving a two base 3' overhang (Arrand, J. R., Myers, P. A., and Roberts, R. J., unpublished observations).

SacII methylase or restriction endonuclease produced in accordance with the present invention is substantially pure and free of the contaminants normally found in restriction endonuclease preparations made by conventional technique. In addition, SacII methylase and restriction endonuclease produced in accordance with the present invention are free of contaminating SacI and SacIII methylase or restriction endonuclease.

BRIEF DESCRIPTION OF THE DRAWINGS

FIGS. 1A and 1B: Scheme for cloning and producing the SacII restriction endonuclease:

FIG. 1A illustrates the procedures for determining the preferred method for cloning and producing the SacII restriction endonuclease.

FIG. 1B illustrates the preferred method for cloning and producing the SacII restriction endonuclease based on actual results presented in FIG. 1A.

DETAILED DESCRIPTION OF THE INVENTION

The present invention relates to recombinant DNA which encodes the SacII restriction endonuclease and modification methylase, as well as to the enzymes produced from such a recombinant DNA. At the onset of the cloning project, it was not known which endonucleases or conditions would be successful in cloning the SacII restriction-modification system, nor where the restriction and modification genes were located within such clones. The cloning results and subsequent mapping, and characterization of the clones described in FIG. 1A and Example I reveal the previously unknown direct pathway for cloning and expressing the SacII restriction-modification system.

More specifically, the cloning of the SacII restriction-modification genes from *Streptomyces achromogenes* into *E. coli* proved to be complicated by the discovery that unlike many other Type II restriction-modification systems, SacII genes do not express well in *E. coli*. Since methylase selection (the identification of methylase clones by their ability to resist and survive SacII digestion) relies on methylase expression, selection for the SacII methylase is not always successful.

Expression was also found to be a problem for the SacII restriction endonuclease gene. Methylase clones from many other Type II restriction-modification systems can be screened for restriction endonuclease activity with in-vitro assays. However, none of the SacII restriction-modification clones expressed endonuclease activity detectable by in vitro assays, such as the assay described in the above-referenced EPO Publication 0193413, even after concentrating crude cell extracts over phosphocellulose columns. In order to determine whether the R gene was present in the M clones, numerous additional steps were required. The steps included: a) cloning *S. anhromogenes* chromosomal DNA on both sides of the M gene (EcoRV and PstI clones), b) subcloning these methylase clones onto a Streptomyces cloning vector and transforming these plasmids into *Streptomyces lividans*. In this manner, the EcoRV methylase clones were found to carry the R gene, whereas the other methylase clone was found not to carry the R gene. In order to obtain overexpression of the SacII restriction endonuclease, smaller subclones were generated in *S. lividans*.

Figure 1B:
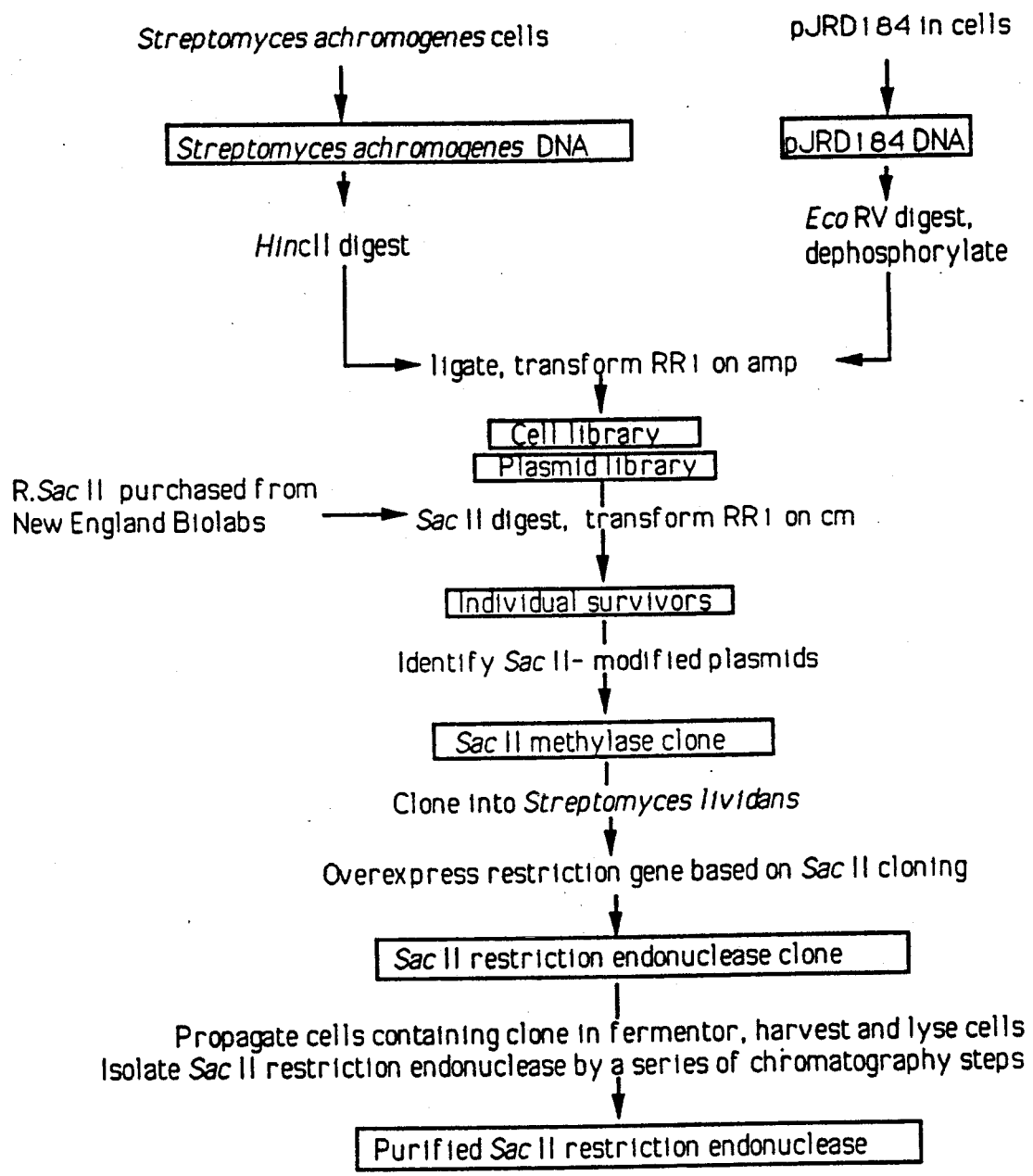

The method described herein by which the SacII restriction gene and methylase gene are preferably cloned and expressed is illustrated in FIGS. 1A and 1B and includes the following steps:

1. *Streptomyces achromogenes* (ATCC No. 12767) is grown in nutrient broth with 68 g/l sucrose, 0.2 g/l MgCl₂, 5 g/l glucose, pH adjusted to 7.2 with NaOH and grown with aeration and agitation. The cells are lysed and the genomic DNA purified by the techniques 262:4770–4777 (1987) and is described in detail in the example.

2. The *S. achromogenes* chromosomal DNA is digested completely and partially with a restriction endonuclease such as PstI. Other restriction enzymes such as ScaI and EcoRV can also be used.

3. The digested DNA's are each ligated to a cloning vector, such as pJRD184 (Davidson, et al., *Gene* 39:299–304 (1984)), which contains at least one SacII site. Other cloning vectors such as pACYC184 and pACYC177 (Chang, ACY, *J. Bact.*, 134:1141–1156 (1978)) can also be used. The resulting mixtures are used to transform an appropriate host such as *E. coli* strain RR1 or K802 cells (ATCC No. 31343 and ATCC No. 33526, respectively). RR1 which are mrr⁻ is the preferred host cell.

4. The DNA/cell mixtures are preferably plated on antibiotic media selective for transformed cells, such as ampicillin or chloramphenicol. After incubation, the transformed cell colonies are collected together to form the primary cell libraries.

5. The recombinant plasmids are purified into from the primary cell libraries to make primary plasmid libraries.

6. The plasmid libraries are then digested to completion in vitro with the SacII restriction endonuclease, which is prepared from *Streptomyces achromogenes* cells using standard purification technique. SacII restriction endonuclease digestion causes the selective destruction of unmodified, non-methylase-containing clones, resulting in an increase in the relative frequency of SacII methylase-carrying clones.

Endonuclease and/or phosphatase may also be added to the digestion to enhance the destruction of non-methylase clones.

7. Identification of SacII methylase clones: The digested plasmid library DNA's are transformed back into a convenient host such as *E. coli* strain RR1 or K802, and transformed colonies are again obtained by plating on antibiotic plates. DNA from individual colonies is analyzed for the presence of the SacII modification gene in the following manner: The plasmid DNA that they carry is purified and incubated in vitro with SacII restriction endonuclease to determine whether it is resistant to digestion by SacII. The plasmid DNA should be completely or substantially resistant to digestion. The total cellular DNA (chromosomal and plasmid) of the clone is also purified and incubated with SacII restriction endonuclease. Further proof that the methylase gene has been cloned involves deleting the insert and checking the remaining vector for presence of intact SacII sites.

8. Once it has been established that the methylase gene has been cloned, the clone is assayed for SacII restriction endonuclease activity. If activity is detected, then the SacII restriction gene is linked to the methylase gene and is present in the clone. In such a case one could then skip to step 15 below. However, in accordance with the present invention, it has been found that even if present, the restriction gene is not expressed without further genetic manipulation as discussed below. The lack of restriction activity indicates that either the restriction gene is not linked to the methylase gene, or it is linked but not cloned intact with the methylase gene, or it is cloned intact but not expressed. In order to determine which of the above three possibilities is the true situation, the cloned fragment is restriction-mapped and deletions are made to determine where the methylase gene lies within the cloned fragment. The information is then used to determine if there is enough DNA on either side of the methylase gene to encode a restriction gene, if it were linked. If there is enough room, the restriction gene is assumed to be not linked, or to be present in the clone but not expressed (and one could skip to step 10). If there is not enough room on both sides of the methylase gene in the cloned DNA to encode a linked restriction gene, as was found for the PstI clone of the present invention, a portion of the methylase gene is used to probe digests of the SacII chromosome to generate a genomic map of the region extending beyond the boundaries of the existing cloned DNA. This data helps identify certain endonucleases that cleave the restriction-modification region into individual fragments that carry the methylase gene as well as larger amounts of adjacent DNA. The exact sizes of the fragments generated by such endonucleases are known from the data as well. Presumably, if the restriction and modification genes are found to be linked, such fragments would also encode the restriction gene.

9. Libraries are constructed by digesting genomic DNA from *S. achromogenes* with restriction endonucleases identified by Southern blot analysis to generate fragments which might encode the intact SacII restriction modification system. These fragments are ligated into an appropriate vector such as pUC19 (ATCC No. 37017). This is used to transform an appropriate host such as *E. coli* strain RR1. Clones carrying the methylase gene and adjacent DNA are identified by colony hybridization using a portion of the methylase clone as a probe. Once isolated, these clones are analyzed for their ability to produce SacII methylase and restriction endonuclease.

10. Identification of restriction gene clones: In accordance with the present invention, it has been found that clones carrying the SacII restriction endonuclease gene cannot be identified by the usual crude cell extract assay because of the low-level expression of the gene in *E. coli*. Therefore, subclones are constructed which can be used to transform a host more closely related to *S. achromogenes* than *E. coli*. The DNA fragments containing the insert DNA are isolated away from the *E. coli* vector and ligated into a Streptomyces cloning vector such as pIJ486 (Ward, J. M. et al., *Mol. Gen. Genet.*, 203:468–478). The ligation mixture can then be used to transform protoplasts of an appropriate host such as *S. lividans* TK24, in accordance with the procedure of Hopwood, D. A., et al., *Genetic Manipulation of Streptomyces, a Laboratory Manual*, the disclosure of which is herein incorporated by reference.

11. The DNA/cell mixtures are preferably plated on regeneration media. Once regenerated the transformants are selected with an antibiotic, such as thiostrepton. After incubation, the transformed cell colonies can be picked and streaked for isolated colonies.

12. The recombinant plasmids are purified from several of the transformants.

13. The plasmids are then digested with SacII and examined on an agarose gel to determine if the clones have any methylase activity. They are also digested with other restriction endonucleases to insure that the correct fragment has been cloned.

14. If the clones have methylase activity, several of these clones are individually grown in rich liquid media. Crude extracts of the methylase clones are prepared and assayed for SacII restriction endonuclease activity.

15. A restriction map is made and different subclones constructed in *E. coli* and in *S. lividans* to determine the location of the intact SacII methylase and restriction endonuclease genes. Each subclone is tested for overexpression of the SacII restriction endonuclease gene.

16. Production: In one preferred embodiment, the SacII methylase or endonuclease may be produced from transformed host cells transformed with one or more plasmid clones carrying the SacII modification gene and the overexpressed restriction gene by propagation in a fermenter in a rich medium containing thiostrepton. The cells are thereafter harvested by centrifugation and disrupted in a French press to produce a crude cell extract containing SacII methylase and restriction endonuclease activity. In another preferred embodiment, the host cell can be pre-protected by transformation with plasmids carrying the methylase gene, followed by introduction of plasmids carrying the endonuclease gene.

17. Purification: The crude cell extract containing the SacII methylase and endonuclease is purified by standard product purification techniques such as affinity-chromatography, or ion-exchange chromatography.

18. The endonuclease so purified is found to be free of other contaminating enzymes including SacI and SacIII, and substantially free of non-specific nucleases.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE I

Cloning of SacII Modification Methylase and Restriction Endonuclease Genes

1. *S. achromogenes* DNA purification: 10 g of frozen *Streptomyces achromogenes* cells (ATCC #12767) were thawed on ice for 1 h, then resuspended in 20 ml of 25% sucrose, 50 mM Tris pH 8.0. 10 ml of 0.25M EDTA pH 8.0, and 6 ml of 10 mg/ml lysozyme in 0.25M Tris pH 8.0 were added. The suspension was kept on ice for 2 h, then lysed by the addition of 24 ml of 1% Triton X-100, 50 mM Tris pH 8.0, 67 mM EDTA and 5 ml of 10% SDS. The solution was extracted with 70 ml of phenol, (previously equilibrated with 0.5M Tris pH 8.0), and 70 ml of chloroform. The emulsion was centrifuged at 10K rpm for 30 min and the viscous upper layer was withdrawn. The layer was reextracted with phenol/chloroform, and the emulsion was again centrifuged to separate the phases. The upper layer was withdrawn and dialyzed against four changes of 10 mM Tris pH 8.0, 1 mM EDTA. The dialyzed solution was then digested with RNase at a final concentration of 100 ug/ml for 1 h at 37° C. The DNA was then precipitated by adding NaCl to a final concentration of 0.4M, overlaying with 0.55 vol of isopropyl alcohol, and spooling the DNA onto a glass rod by mixing the phases together. The DNA was resuspended in DNA buffer (10 mM Tris pH 8.0, 1 mM EDTA) and stored at 4° C.

2. Partial digestion of *S. achromogenes* DNA: 200 ug of *S. achromogenes* DNA was diluted into 2 ml of restriction endonuclease digestion buffer (10 mM Tris pH 7.5, 10 mM $MgCl_2$, 10 mM 2-mercaptoethanol, 100 mM NaCl). The solution was dispensed into 5 tubes, 300 ul into the first tube and 150 ul into each of the remaining tubes. 210 U of PstI (10 ul) was mixed into the first tube to achieve 7 U enzyme/ug of DNA; 150 ul was withdrawn and transferred to the second tube (3.5 U/ug). 150 ul was then withdrawn from the second tube and transferred to the third tube, and so on, each transfer effecting a 2-fold serial dilution of PstI. The tubes were incubated for 1 h at 37° C., then heated for 15 min at 72° C. to stop the reactions. 5 ul from each tube was analyzed by agarose gel electrophoresis. Tubes in which moderate, but incomplete, digestion had occurred were combined. Two additional digestion series were performed in a similar manner using Sau3A and EcoRI.

3. Ligation and transformation: 6 ug (60 ul) of PstI-digested *S. achromogenes* DNA was mixed with 3 ug (6 ul) of PstI-cleaved and dephosphorylated pJRD184 (obtained from Labofina s.a., of Feluy, Belgium. pJRD184 is described in the publication, Davidson et al., *Gene* 39:299-304, (1984)). 20 ul of 500 mM Tris pH 7.5, 100 mM $MgCl_2$, 100 mM DTT, 5 mM ATP, and 106.5 ul of sterile distilled water were added to bring the volume to 192.5 ul. 7.5 ul of T4 DNA ligase was added and the solution was incubated at 17° C. overnight. The solution was sterilized by extraction with 10 ul of chloroform, then clarified by microcentifugation for 15 s. 70 ul of the ligation solution was mixed with 1.0 ml of 50 mM NaCl, 5 mM Na3Citrate, 67 mM $CaCl_2$ and 2.0 ml of ice-cold, competent *E. coli* K802 (ATCC No. 33526) cells were added. The solution was incubated at 44° C. for 5 min, then 12.5 ml of Luria-broth (L-broth) was added and incubation was continued at 37° C. for 3 h. Similar ligations were also set up between the Sau3A digest of *S. achromogenes* DNA and BamHI-digested pJRD184, and between the EcoRI digest of *S. achromogenes* DNA and EcoRI-digested pJRD184. The additional ligations were also transformed into *E. coli* K802.

4. Primary cell libraries: The transformed cultures were gently centrifuged, the supernatants were discarded, and the cells from each culture were resuspended in 1.0 ml of Luria-broth. 200 ul portions of the resuspended cells were plated onto Luria-agar (L-agar) plates containing 100 ug/ml ampicillin. The plates were incubated overnight at 37° C. The colonies that grew up were collected into three pools, one for each ligation, by flooding each plate with 1.5 ml of 10 mM Tris pH 7.5, 10 mM $MgCl_2$, and scraping the colonies together.

5. Primary plasmid libraries: 2.0 ml of each cell library was inoculated into 500 ml of L-broth containing 100 ug/ml ampicillin. The cultures were shaken overnight at 37° C. then centrifuged at 4K rpm for 5 min. The supernatants were discarded and the cell pellets were resuspended in 10 ml of 25% sucrose, 50 mM Tris pH 8.0, at room temperature. 5 ml of 0.25M EDTA, pH 8.0, and 3 ml of 10 mg/ml lysozyme in 0.25M Tris pH 8.0 was added to each. The solutions were kept on ice for 1 h, then 12 ml of 1% Triton X-100, 50 mM Tris pH 8.0, 67 mM EDTA was added to each, and the suspensions were gently swirled to induce cell lysis. The lysed mixtures were transferred to a 50 ml tubes and centrifuged for 45 min. at 17K rpm, 4° C. The supernatants were removed with a pipette. 20.0 gm of solid CsCl was weighed into three 50 ml plastic screw-cap tubes and 22.0 gm of each supernatant was pipetted into each tube and mixed. 1.0 ml of 5 mg/ml ethidium bromide in 10 mM Tris pH 8.0, 100 mM NaCl, 1 mM EDTA was added to each tube. Each of the solutions was transferred to two ⅝ in.×3 in. centrifuge tubes and spun in a Beckman Ti70 rotor for 42 h at 44K rpm, 17° C. To collect the plasmid DNA in each tube, they were illuminated with ultraviolet light and the lower of the two fluorescent bands was collected by syringe. The ethidium bromide was removed from each of the collected bands by extracting four times with an equal volume of CsCl-saturated, isopropanol. The extracted solutions were dialyzed against 4 changes of DNA buffer, then the nucleic acids were precipitated overnight at −20° C. by the addition of 2 vol of isopropanol and NaCl to a final concentration of 0.4 M. The solutions were centrifuged for 15 min at 15K rpm, 0° C., the supernatants were discarded, the pellets were air-dried for 15 min and then each was dissolved in 500 ul of 10 mM Tris pH 7.5, 1 mM EDTA and stored at −20° C. The plasmid DNA concentrations were approximately 100 ug/ml.

6. Digestion of plasmid pool: 1 ug quantities of the plasmid libraries in 100 ul of 10 mM Tris pH 7.5, 10 mM $MgCl_2$, 10 mM 2-mercaptoethanol, 10 mM NaCl, were digested with 0, 20, and 40 U of SacII restriction endonuclease at 37° C. for 2 h.

Following the digestions, 1.4 U (1.4 ul) of CIP (calf intestine phosphatase) were added to each reaction and incubated for 15 min. at 37° C. and then for 15 min. at 56° C. An additional 1.4 U were added to each reaction and the temperature steps repeated. After completion of the dephosphorylating reactions, 20 ul (0.2 ug) of each library was transformed into *E. coli* K802. The mixtures were plated onto Luria-agar plates containing 100 ug/ml ampicillin, and incubated overnight at 37° C. Digestion with SacII restriction endonuclease reduced the number of transformants approximately 103-fold.

7. Analysis of survivors: Between ten and thirty-five colonies were picked from among the survivors of each library. Each colony was inoculated into 10 ml of Luria-broth containing 100 ug/ml ampicillin, and grown overnight at 37° C. Each of the plasmids present in the seventy-seven isolates was prepared by the following miniprep purification procedure, adapted from Birnboim and Doly, *Nucleic Acids Res.* 7:1513 (1979):

Miniprep purification procedure: Each culture was centrifuged at 8 Krpm for 5 min; the supernatant was discarded and the cell pellet was resuspended in 1.0 ml of 25 mM Tris, 10 mM EDTA, 50 mM glucose, pH 8.0, containing 1 mg/ml lysozyme. After 10 min at room temperature, 2.0 ml of 0.2M NaOH, 1% SDS was added to each tube; the tubes were shaken to lyse the cells, then they were placed on ice. Once the solutions had cleared, 1.5 ml of 3M sodium acetate, pH 4.8, was added to each and shaken. The precipitates that formed were spun down at 15K rpm, 4° C. for 10 min. Each supernatant was poured into a centrifuge tube containing 3 ml of isopropanol and mixed. After 10 min at room temperature, the tubes were spun at 15K rpm for 10 min to pellet the precipitated nucleic acids. The supernatants were discarded and the pellets were air-dried at room temperature for 30 min. Once dry, the pellets were resuspended in 850 ul of 10 mM Tris, 1 mM EDTA, pH 8.0. 75 ul of 5M NaCl was added to each and the solutions were transferred to Eppendorf tubes containing 575 ul of isopropanol, and again precipitated for 10 min at room temperature. The tubes were then spun for 45 s in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 h at 37° C. to digest the RNA. The DNA was precipitated once more by the addition of 50 ul of 5M NaCl followed by 350 ul of isopropanol. After 10 min at room temperature, the DNA was spun down by centrifugation for 45 s, the supernatants were discarded and the pellets were redissolved in 150 ul of 10 mM Tris 1 mM EDTA, pH 8.0. The plasmid minipreps were subsequently analyzed by digestions with SacII, PstI, EcoRI and Sau3A.

8. Identification of a SacII methylase clone: Seventy-six of the seventy-seven plasmids that were analyzed were found to be sensitive to SacII-digestion and to carry diverse fragments of *S. achromogenes* DNA. These plasmids were spurious and they were discarded. The remaining plasmid was found to be resistant to SacII-digestion and to carry a single 5.9 kb PstI fragment. However, the clone failed to synthesize the SacII endonuclease. The 5.9 kb fragment was excised out of the pJRD184 plasmid and ligated into pUC19 for more convenient manipulations. This plasmid was designated pMMsacIIM 11-4.

9. Location of the methylase gene within the 5.9 kb PstI fragment: We assumed that the SacII endonuclease gene was located next to the SacII methylase gene in the chromosome of *S. achromogenes*. Extensive mapping and subcloning DNA fragments of the original clone with restriction enzymes revealed that the methylase was located at one extreme end of the original 5.9 kb fragment. This information suggested that possibly the DNA encoding for the SacII endonuclease gene was not present on the 5.9 kb fragment. At this point, the distance between the two genes, the exact size of the genes, and whether or not they were linked was not known. The lack of SacII endonuclease activity in the clone indicated that the restriction gene was either not present in the clones, or was present but not expressed. In the event that the entire restriction gene was not present, the cloning of larger regions of DNA adjacent to the methylase gene was achieved as follows in steps 10–13. in the event that the larger clones still did not express the SacII restriction endonuclease, these clones would be subcloned into Streptomyces to determine if a more closely related host would express the restriction endonuclease gene (steps 14–17).

10. A genomic map of the adjacent regions was determined using the Southern blot technique (Southern, E., *J. Mol. Bio.*, 98:503 (1975)). The pMMsacIIM11-4 plasmid DNA was purified and nick-translated to prepare a hybridization probe for Southern blots. 0.5 ug (5 ul) of plasmid DNA was mixed with 1.5 ul of 10× nick-translation buffer (0.5M Tris.HCl, pH 7.5, 50 mM $MgCl_2$, 10 mM 2-mercaptoethanol); 1 ul of dATP, dCTP, dGTP, dTTP mix (500 pMole of each nucleotide in dH20); 5 ul of [$^{32}$P]-dATP (Amersham; 800 Ci/mMol, 20 mCi/ml); 2 ul (20 U) of *E. coli* DNA polymerase I (New England Biolabs); and 1 ul of DNase I (1.0 ug/ml). The mixture was incubated at 16° C. for 2 h, then the reaction was stopped by the addition of 100 ul of 10 mM EDTA, pH 8.0.

The Southern blot was prepared as follows: *S. achromogenes* DNA was digested separately with the restriction endonuclease FspI, ScaI, KonI, PvuII, BalI, EcoRV, XmnI, StuI, DraI and SsoI. The digests were electrophoresed on a 1.0% agarose gel. The gel was soaked in 0.25M HCl for 15 min; 0.5M NaOH, 1 M NaCl for 30 min; and then in 1M Tris.HCl pH 7.5, 3M NaCl for 30 min. A nitrocellulose sheet was soaked in water for 1 h, then briefly immersed in 5× SSC (0.75M NaCl, 75 mM $Na_3$Citrate). The sheet was applied to the surface of the gel and backed with chromatography paper (Whatman) to act as a wick. The sandwich was weighted down and transfer of the gel contents to the nitrocellulose sheet was allowed to proceed at room temperature for 4 h. The sheet was then baked in a vacuum oven at 80° C. for 1 h. to fix the transferred DNA fragments to the nitrocellulose support. The sheet was transferred to a plastic bag containing 15 ml of a solution composed of 3 ml of 10 gm/L Ficoll, 10 gm/L polyvinylpyrrolidone, 10 gm/L bovine serum albumin; 4.5 ml of 3M NaCl, 0.3M $Na_3$Citrate; 1.5 ml 10% SDS; 3 ml 10% dextran sulfate; 3 ml water, and prehybridized by incubating at 63° C. for 1 h. The entire radioactive probe was added to the bag, and incubation was continued at 65° C. overnight. The nitrocellulose sheet was then washed at room temperature three times for 5 minutes in 2× SSC, 0.5% SDS. This step was followed by three 20 minute washes at 65° C. in 2× SSC, air-dried then autoradiographed overnight. The probe hybridized to a single, 14 kb band in the FsoI-digest, to a 9.4 kb band in the ScaI-digest, to a 8.9 kb band in the EcoRV-digest and to a 14 kb band in the StuI-digest. These bands were judged to be of suitable size for cloning, and to be likely to contain the SacII endonuclease gene as well as the SacII methylase gene.

11. Preparation of *S. achromogenes* libraries: Four new libraries consisting of *S. achromogenes* DNA inserted into the plasmid pUC19, were prepared in *E. coli* RR1. In separate reactions, *S. achromogenes* DNA was digested to completion with FsoI, ScaI, EcoRV, and StuI. The reactions were stopped by heating to 72° C. for 15 min. 1 ug of each of the digested DNA's was combined with 1 ug of HincII-cleaved and dephosphorylated pUC19 DNA (ATCC No. 37017). 3 ul of 500 mM Tris pH 7.5, 100 mM MgCl$_2$, 100 mM DTT, 8 mM ATP was added, and the vol of each reaction was brought to 30 ul with water. 3 ul of T4 DNA ligase was added to each mixture, and ligation was carried out at 16° C. overnight. The ligations were terminated by extraction with 10 ul of chloroform, and then the mixtures were transformed separately into competent E. coli RR1. The transformation mixtures were plated onto Luria-agar plates containing 100 ug/ml ampicillin. The plates were incubated overnight at 37° C.

12. Isolation of overlapping SacII methylase gene fragments: Colonies were screened for hybridization to the 5.9 kb PstI fragment containing the SacII methylase gene. The colonies representing the new libraries prepared as described in Section 13, above, were transferred to nitrocellulose filters by contact-lifts. The filters were immersed in 0.5M NaOH, 2M NaCl for 30 s; 0.5M Tris.HCl, pH 7.5, 3M NaCl for 1 min; 0.3M NaCl, 0.03M Na$_3$Citrate, 0.1% SDS for 5 s; 0.3M NaCl, 0.03M Na$_3$Citrate for 10 s. The filters were air-dried, and then they were baked in a vacuum-oven at 80° C. for 30 min. The filters were prehybridized, and then hybridized (using the procedure described in Section 10) with the 2.0 kb SacII methylase gene probe.

Preparation of SacII methylase gene probe: A 2.0 kb BolII to EcoRV subfragment of the 5.9 kb PstI insert carried in pMMsacIIMII-4 was gel-purified and nick-translated. 10 ug of the plasmid DNA was incubated at 37° C. for 1 h in 10 mM Tris pH 7.5, 10 mM MgCl$_2$, 150 mM NaCl, 10 mM 2-mercaptoethanol with 120 U each of BolII and EcoRV. The digest was fractionated by gel electrophoresis on a 1.0% Tris-acetate agarose gel. The gel was run for 2.5 h, at 100 mA, then illuminated with long-wave UV light and the 2.0 kb band was cut out of the gel and transferred to a syringe. The gel slice was extruded through an 18 gauge needle into a 5 ml centrifuge tube. The tube was centrifuged at 43K rpm for 45 min at 25° C. in a Beckman SW 50.1 rotor. The supernatant was collected and the DNA was precipitated at −70° C. for 1 h by the addition of NaCl to 0.5M, and 2 vol of isopropanol. The precipitated DNA was resuspended in 500 ul of 10 mM Tris.HCl pH 8.0, 1 mM EDTA. The DNA was nicked translated using the procedure outlined in Section 10. The filters were air-dried, and then they were autoradiographed overnight.

13. Identification of new SacII methylase gene clones: Approximately 4,000 colonies were screened from the EcoRV-library; of these, six colonies hybridized strongly to the probe. The six clones were analyzed; two were found to carry the sought-after, 8.9 kb EcoRV-fragment, and the other four were found to be spurious. Approximately 8,000 colonies were screened from the ScaI-library and four of fifteen strongly-hybridizing colonies from this library contained the 9.4 kb ScaI fragment There were no strongly-hybridizing colonies found from the screening of the FsoI and StuI-libraries (∼5,000 colonies screened/library). One positive clone from each of the EcoRV and ScaI-libraries was retained and analyzed The clone from the EcoRV-library, designated pMMsacIIRM3, was found to have 6.4 kb flanking the side of the SacII methylase gene which had the least DNA in the original SacII methylase clone (recalling the SacII methylase gene was at one extreme end in the original clone.). The analysis of the clone from the ScaI-library, designated pMMsacIIRM8, determined that there is 1.0 kb flanking one side of the SacII methylase and 3.0 kb flanking the other side. Extracts of the clones were assayed for restriction endonuclease activity and no activity was detected from either clone.

Figure 2:
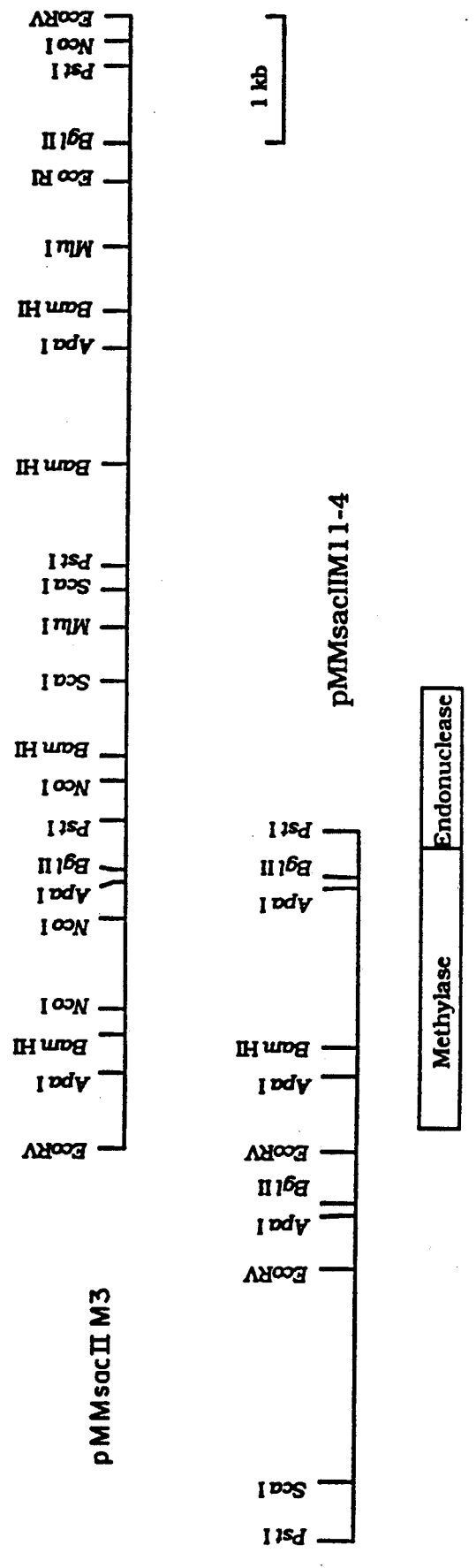
FIG. 2 is a restriction map of the 8.9 kb EcoRV fragment and the 5.9 kb PstI fragment of *Streptomyces achromogenes* that has been cloned by SacII methylase selection.

14. Subcloning the SacII methylase clones into S. lividans: With the recovery of the new clones, there was now enough DNA cloned on both sides of the methylase gene to encode a restriction endonuclease gene, if it were linked, regardless of which side encoded the linked gene. However, none of the clones expressed any restriction endonuclease activity. With still no proof that the two SacII restriction-modification genes were linked, the clones were subcloned into S. lividans, a species more closely related to S. achromogenes than E. coli. 10 ul (1.5 ug) of pMMsacIIRM3 (the EcoRV methylase clone in pUC19, FIG. 2) was digested in 50 ul of 10 mM Tris pH 7.5, 10 mM MgCl$_2$, 100 ug/ml bovine serum albumin, 100 mM NaCl containing 20 U of EcoRI and 20 U of HindIII at 37° C. for 1 h. The entire volume was electrophoresed in a 0.7% agarose gel for 2 h. The 7.5 kb EcoRI-HindIII restriction fragment was electrophoresed into DEAE anion exchange paper for two h. The paper was washed two times in 150 ul of a buffer containing 0.1M NaCl, 10 mM Tris pH 8.0, and 1 mM EDTA. Subsequently, the DNA was eluted from the paper by washing the paper four times with 75 ul of a buffer containing 1.0M NaCl, 10 mM Tris pH 8.0 and 1 mM EDTA. The resulting solution containing the DNA fragment was extracted with 300 ul phenol/-chloroform followed by extraction with 300 ul chloroform and precipitated with 1 ml absolute ethanol by placing in a dry ice/ethanol bath for 15 min. The DNA was pelleted at 14k rpm for 5 min. The pellet was rinsed with 70% ethanol, air dried and resuspended in a final volume of 10 ul 10 mM Tris pH 8, and 1 mM EDTA. 9 ul (0.5 ug) of the EcoRI-HindIII purified DNA fragment were ligated to 1 ul (0.2 ug) of EcoRI-HindIII -cleaved and dephosphorylated pIJ486 (obtained from Hopwood, D. A. of Norwich, England. pIJ486 is described in the publication, Ward, J. M. et al., Mol. Gen. Genet. 203:468–478.) in 50 ul 1× ligation buffer containing 1 ul T4 DNA ligase (400 U) at 12° C. overnight. 10 ul of the ligation mix was added to approximately 4×10$^9$ S. lividans TK24 (obtained from Hopwood, D. A. TK24 is described in Hopwood, D. A., et al., *Genetic Manipulation of Streptomyces, a Laboratory Manual*) protoplasts, prepared as described in Hopwood D. A., et al., ibid, in P Buffer [103 g Sucrose, 0.25 g K$_2$SO$_4$, 2.02 g MgCl$_2$.6H$_2$O, 2 ml Trace elements solution, and ·distilled water to 800 ml. 80 ml aliquots are dispensed and autoclaved. Before use add to each 80 ml: 1 ml 0.5% KH$_2$PO$_4$, 10 ml 3.68% CaCl2.2H$_2$O and 10 ml 5.73% TES buffer pH7.2. Trace elements solution per liter: 40 mg ZnCl$_2$, 200 mg FeCl$_3$.6H$_2$O, 10 mg CuCl$_2$.4-H$_2$O, 10 mg MnCl$_2$.4H$_2$O, 10 mg Na$_2$B$_4$O$_7$.10H$_2$O and 10 mg (NH$_4$)6Mo$_7$O$_{24}$.4H$_2$O] 0.5 ml of 25% polyethylene glycol 1000 was added to the protoplast/DNA mixture. This was drawn up and down 3 times in a 1 ml pipette. 0.1 ml of the transformation mix was plated on each of six R2YE plates [103 g Sucrose, 0.25 g K$_2$SO$_4$, 10.12 g MgCl$_2$.6H$_2$O, 10 g Glucose, 0.1 g Difco Casaminoacids and 800 ml H$_2$O, 80 ml of this solution are mixed with 2.2 g Difco agar and autoclaved. To prepare the plates the base agar solution is melted and the following sterile solutions are added: 1 ml 0.5% KH$_2$PO$_4$, 8 ml 3.68% CaCl$_2$.2H$_2$O, 1.5 ml 20% L-proline 10 ml 5.73% TES buffer pH7.2, 0.2 ml Trace elements solution, and 0.5ml 1N NaOH. The plates are poured and dried in a laminar flow hood for at least 1 h.]. The plates were overlayed after incubating overnight at 30° C. with 1.0 ml of an aqueous solution of thiostrepton (0.5 mg/ml). The plates were returned to 30° C. for 3 to 4 days until the colonies have grown.

15. Analysis of transformants: 6 of the surviving colonies obtained from selection 15 were streaked on R2YE plates containing 5 ug/ml thiostrepton for isolated colonies. Once grown, these were used to inoculate 5 ml of TSB with 5 ug/ml thiostrepton. These cultures were incubated at 30° C. with aeration for 24 h. Minipreps were done on 0.5 ml of the cultures. This procedure is identical to the procedure described by Birnboim and Doly (Nucleic Acids Research, 7:1513 (1979)) with the exception that a 30 minute incubation in 4 mg/ml of lysozyme, 50 mM Glucose, 25 mM Tris pH8.0, and 10 mM EDTA at 37° C. is necessary before adding the NaOH-SDS solution 10 ul of the miniprep DNA was analysed by running on an 0.7% agarose gel. 3 of the 6 clones appeared to be larger than pIJ486. Spores from these three isolates were harvested and used to inoculate 500 ml TSB +Thiostrepton. CsCl plasmid prep was prepared on 450 ml of the culture following a scaled up (20×) version of Procedure 3 P. 93 in Hopwood et al. ibid. The resulting pellet was resuspended in 17 ml 10 mM Tris pH 8.0, 1 mM EDTA, 18.7 g CsCl and 0.44 ml ethidium bromide (5 mg/ml). The solution was transferred to two ⅝ in.×3 in. polyallomer centrifuge tubes and sealed. These tubes were centrifuged in a Beckman Ti70 rotor for 44k rpm for 48 h, 17° C. To collect the plasmids, the tops of the tubes were pierced with a scalpel and the lower of the two fluorescent DNA bands was collected by syringe under ultraviolet light. The lower band from both tubes was combined into a 15 ml Corex tube and the ethidium bromide was removed by adding an equal volume of water and three volumes of ethanol. After 2 h at −20° C. the DNA was pelleted by spinning at 12k rpm for 20 min. The pellet was resuspended in 2 ml 10 mM Tris pH 8.0, 1 mM EDTA. 50 ul of 8M LiCl was added and the DNA was extracted with phenol/chloroform followed by a chloroform extraction. The DNA was precipitated by adding 3 volumes ethanol to the aqueous solution as described above. The pellet was resuspended in 500 ul 10 mM Tris pH 8.0, 1 mM EDTA. The purified plasmid was digested with EcoRI and HindIII to confirm the presence of the insert as well as with SacII to determine if the subclone in S. lividans had any SacII methylase activity. All three subclones were apparently identical having the correct construction as well as having methylase activity i.e., were unable to be digested with the SacII endonuclease 50 ml of the culture used to make the plasmid prep was washed with 10.3% sucrose the pellet was frozen at −70° C. Upon thawing the pellet was resuspended in 3 ml/g of wet cell weight with a solution of 50 mM Tris pH 8, 10 mM 2-mercaptoethanol and 1 mM PMSF. After sonication on ice the debris were removed by centrifugation at 16k rpm for 45 min. The supernatant was assayed for SacII restriction endonuclease activity. These subclones are denoted pEGsacIIRM1-32, 1-34 and 1-36 (FIG. 3) in S. lividans had $2 \times 10^5$ U/g SacII endonuclease activity, approximately the same level as that observed in S. achromogenes.

Figure 3:
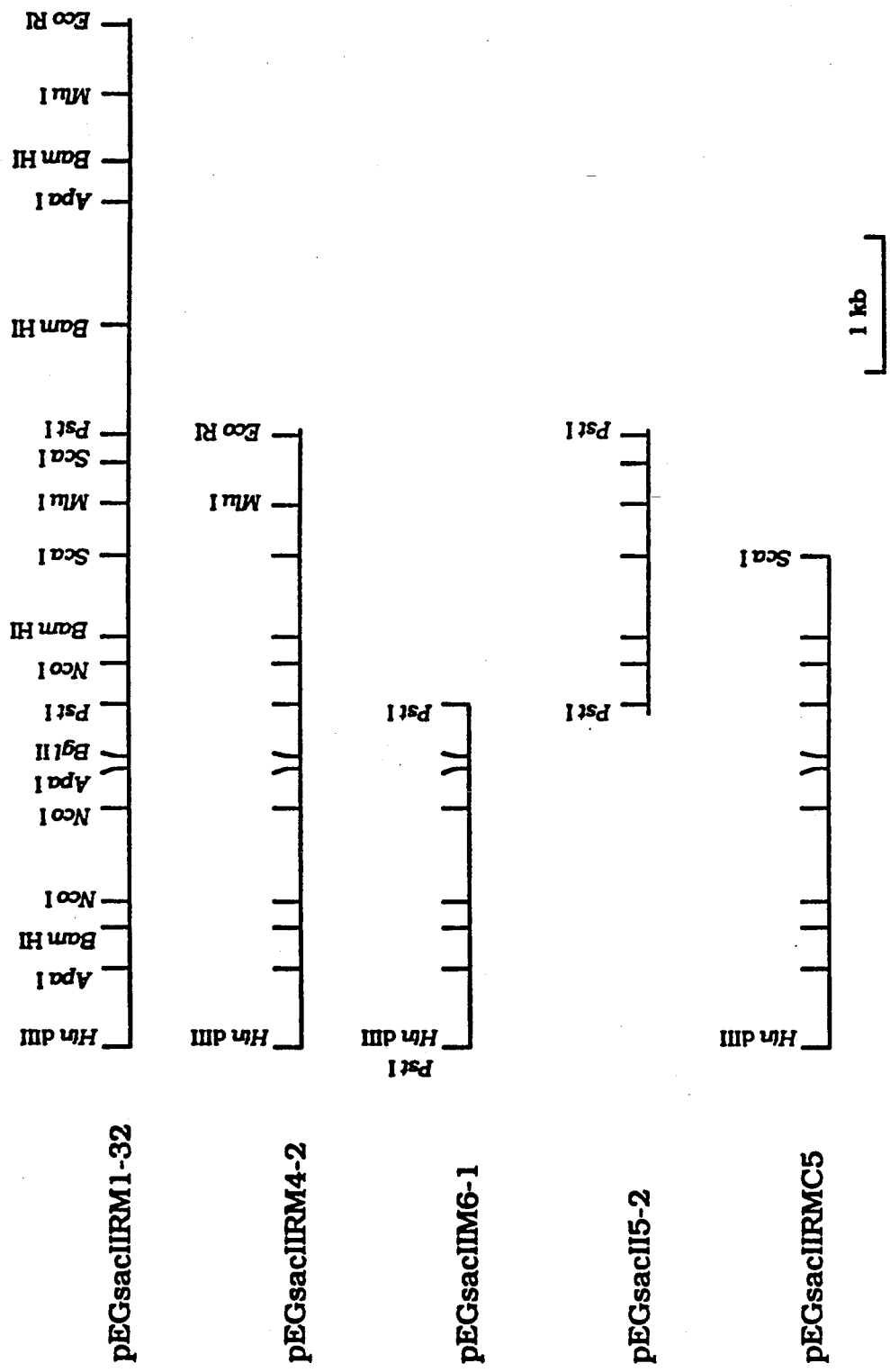
FIG. 3 is a restriction map of several subclones made on pIJ486 in *Streptomyces lividans*.

16. Determining the location of the SacII restriction endonuclease gene: Further subcloning of the EcoRV fragment was done in S. lividans to determine the approximate location of the SacII restriction endonuclease gene. An MluI deletion was constructed denoted pEGsacIIRM4-2 (FIG. 3) which had both endonuclease at a level of $8.5 \times 10^5$ U/g and methylase activity. Two PstI fragments were cloned individually into pIJ486. Only the leftward PstI subclone (pEGsacIIM6-1) displayed SacII methylase activity. Neither subclone gave SacII endonuclease activity, indicating that the SacII endonuclease gene spans that PstI site (FIG. 3).

Figure 4:
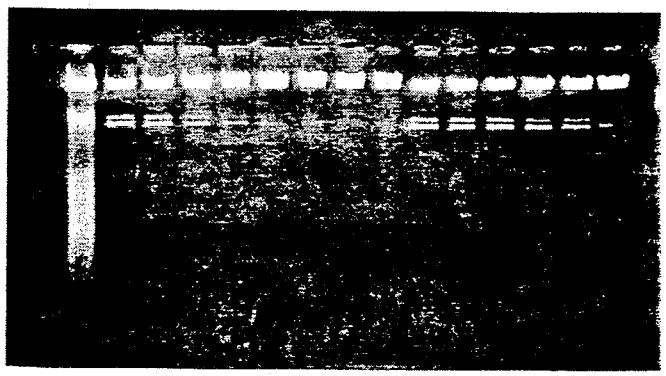
FIG. 4 is a photograph of an agarose gel illustrating SacII restriction endonuclease activity obtained from the cell extract of NEB No. 673.

17. Overexpression of the SacII restriction endonuclease. Another subclone that was constructed was with the ScaI-HindIII fragment (FIG. 3). The DNA fragment first had to be ligated into the SmaI-HindIII sites of pUC19 and transformed into E. coli ED8767 to obtain useful restriction sites for cloning into pIJ486. This subclone, pEGsacIIMC4A, in E. coli showed methylase activity but no endonuclease activity was detected. The relevant fragment was cut out of the pUC19 subclone with EcoRI and HindIII and ligated into EcoRI-HindIII digested pIJ486. S. lividans TK24 transformants which carried this recombinant plasmid, pEGsacIIRMC5, showed SacII methylase activity. When this strain, denoted NEB No. 673, was assayed for SacII restriction endonuclease activity, it showed activity at a level of $4 \times 10^7$ U/g. In FIG. 4, 500 ul of XbaI-digested φC31 DNA was prepared in 1× NEB Buffer 4 (20 mM Tris, 10 mM Mg acetate, 50 mM K acetate, and 1 mM DTT) 50 ul was placed in two tubes and 25 ul was placed in each of 7 tubes. Additionally, 50 ul was placed in one tube and 25 ul in each of 5 tubes to be used as controls. 1 ul of crude cell extract (from cells containing the clone) was added to the first 50 ul tube and mixed. 1 ul was transferred to the second 50 ul tube and mixed, then 25 ul from that tube was transferred to a third tube (containing 25 ul) and mixed, and so on, until six such 1:2 dilutions had been performed using the first seven tubes. For the control, 1 ul (20 units) SacII endonuclease was added to the first control tube, and five 1:2 dilutions (transfer of 25 ul) were carried out among the five control tubes. All tubes were incubated at 37° C. for one hour. 25 ul from each tube was analyzed by gel electrophoresis.

Comparing the control with the crude cell extract of the clone, there are an estimated 40,000,000 units of SacII activity per gram of clone cells. A sample of NEB No. 673 has been deposited at the American Type Culture Collection on Sept. 4, 1990 and bears ATCC designation No. 68391.

18. SacII modification methylase and endonuclease were produced from clones NEB No. 673, carrying the SacII modification gene and the overexpressed restriction gene by propagation in a fermenter in a rich medium containing thiostrepton. The cells were thereafter harvested by centrifugation and 337 g were diluted 1:3 in 0.3M NaCl SD pH 7.7 (10 mM KPO$_4$, 0.1 mM EDTA, 10 mM 2-mercaptoethanol) and disrupted in a French press to produce a crude cell extract containing SacII methylase and restriction endonuclease activity.

19. The SacII restriction endonuclease was prepared from the crude cell extract containing the SacII methylase and endonuclease by loading on a DEAE-Sepharose column (5 cm×17 cm with a bed volume of 333 ml) which had been equilibrated with 0.3M NaCl SB pH 7.7. This was washed with 500 ml 0.2M NaCl SB pH 7.0. The flow-through and the washes were diluted up to 3 l with this same buffer. This was loaded on a Heparin-Sepharose column (4 cm×14 cm with a bed volume of 176 ml). After loading the sample the column was washed with 250 ml 0.2M NaCl SB pH 7.0. To elute the protein, a gradient was run from 0.2M NaCl to 1.2 M NaCl in SB pH 7.0. The pooled fractions (300 ml) containing endonuclease activity were dialyzed against 0.05M NaCl SB pH 7.8. This was loaded on to a DEAE-Sepharose column (2.5 cm×19 cm with a bed volume of 93 ml) which had been equilibrated with 50 mM NaCl SB pH7.8. Once loaded the column was washed with the same buffer. The endonuclease was eluted from the column with a gradient run from 50 mM NaCl to 0.8M NaCl in SB pH 7.8. The fractions with the peak of activity were collected and dialyzed against storage buffer (50 mM KCl, 10 mM Tris-HCl pH 7.4, 0.1 mMEDTA, 1 mM DTT, 200 ug/ml BSA and 50% glycerol and stored at $-20°$ C. The total yield once purified was $3 \times 10^7$U.

The SacII endonuclease obtained from this purification was substantially pure and free of non-specific endonuclease and endonucleases, and was entirely free from contamination with SacI and SacIII endonuclease.

The purity of the SacII restriction endonuclease preparation was checked by looking at the following criteria: 1) Litigation: 95% of the DNA fragments produced by an 10-fold overdigestion were ligated with T4 DNA Ligase (at a 5'termini concentration of 1-2 uM at 16° C.). Of these ligated fragments, 95% were able to be recut. 2) Prolonged digestion: A 50 ul reaction containing 1 ug of DNA and 80 U of enzyme incubated for 16 hours resulted in the same pattern of DNA bands as a reaction produced in 1 h with 1 U of enzyme. 3) Endonuclease activity: Incubation of 100 U for 4 hours at 37° C. in 50 ul assay buffer (50 mM K acetate, 20 mM Tris acetate, 10 mM mg acetate, 1 mM DTT pH 7.9) with 1 ug sonicated 3H DNA (105 cpm/ug) released 0.15% radioactivity. 4) Endonuclease contamination: Incubation of 80 U with 1 ug pBR322 DNA which has no SacII sites (4 hours at 37° C. in 50 ul) gave 20% concentration to RFII.

What is claimed is:

1. A method for cloning DNA for a SacII restriction endonuclease comprising;
    a) purifying DNA from *Streptomyces achromogenes* ATCC No. 12767;
    b) digesting the purified DNA with EcoRV to form DNA fragments;
    c) ligating the DNA fragments into the cloning vector pJRD184;
    d) transforming a host cell with the cloning vector of step c) to form a cell library;
    e) purifying recombinant vectors from the cell library to form a plasmid library;
    f) contacting the plasmid library of step e) with SacII to form a digestion pool, transforming the digestion pool into a host cell, and screening for the presence of one or more cloning vectors containing DNA coding for a SacII methylase;
    g) subcloning the DNA obtained in step f) which contains DNA coding for SacII methylase into a Streptomyces compatible cloning vector;
    h) transforming *Streptomyces lividans* host cell with the cloning vector of step g); and
    i) screening the transformants of step h) for the presence of DNA coding for a SacII restriction endonuclease by identifying transformants which produce the SacII restriction endonuclease.

2. The method of claim 1, wherein the Streptomyces compatible cloning vector is pIJ4896.

3. A method of producing SacII restriction endonuclease comprising;
    a) purifying DNA from *Streptomyces achromogenes* ATCC No. 12767;
    b) partially digesting the purified DNA with EcoRV to form DNA fragments;
    c) ligating the DNA fragments into the cloning vector pCU19;
    d) transforming a host cell with the cloning vector of step c) to form a cell library;
    e) purifying recombinant vectors from the cell library to form a plasmid library;
    f) contacting the plasmid library of step e) with SacII to form a digestion pool, transforming the digestion pool into a host cell, and screening for the presence of one or more cloning vectors containing DNA coding for a SacII methylase;
    g) subcloning the DNA obtained in step f) which contains DNA coding for SacII methylase into a Streptomyces compatible cloning vector;
    h) transforming *Streptomyces lividans* host cell with the cloning vector of step g);
    i) screening the transformants of step h) for the presence of DNA coding for a SacII restriction endonuclease by identifying transformants which produce the SacII restriction endonuclease; and
    j) culturing the transformants of step i) under conditions suitable for expression of the SacII restriction endonuclease.

4. Isolated DNA consisting essentially of DNA coding for the Sac II restriction endonuclease, wherein the isolated DNA is endogenous to *Streptomyces achromogenes* ATCC Accession No. 12767.

5. The isolated DNA of claim 4, wherein the DNA is obtained from the vector pEGsacIIRMC5 ATCC Accession No. 68391.

6. A recombinant DNA vector comprising a vector into which a DNA segment coding for the Sac II endonuclease produced by *Streptomyces achromogenes* ATCC Accession No. 12767 has been inserted.

7. The isolated DNA of claim 4, further comprising DNA coding for the SacII modification methylase.

8. The isolated DNA of claim 6, wherein the DNA is obtained from the vector pEGsacIIRMC5, ATCC Accession No. 68391.

9. A cloning vector which comprises the isolated DNA of claim 8.

10. The cloning vector of claim 9, wherein the cloning vector comprises pEGsacIIRMC5.

11. A host cell transformed by the cloning vector of claims 1, 9 or 10.

12. A method of producing a Sac II restriction endonuclease comprising culturing a host cell transformed with the vector of claims 1, 9 or 10 under conditions suitable for expression of said endonuclease.

* * * * *